US00PP31336P2

(12) United States Plant Patent
Smit

(10) Patent No.: US PP31,336 P2
(45) Date of Patent: Jan. 7, 2020

(54) ALOE PLANT NAMED 'EC-ALOE-1801'

(50) Latin Name: *Aloe hybrida*
Varietal Denomination: EC-ALOE-1801

(71) Applicant: Obed Smit, Sappemeer (NL)

(72) Inventor: Obed Smit, Sappemeer (NL)

(73) Assignee: Eden Collection BV (NL)

( * ) Notice: Subject to any disclaimer, the term of this patent is extended or adjusted under 35 U.S.C. 154(b) by 0 days.

(21) Appl. No.: 16/350,693

(22) Filed: Dec. 18, 2018

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Aloe* cultivar named 'EC-ALOE-1801' is disclosed, characterized by green leaves with a distinctive red coloration to the marginal serration. Leaves are upright with a slight backward arch in the apical section. The new variety is an *Aloe*, typically produced as a garden or container plant.

3 Drawing Sheets

Latin name of the genus and species: *Aloe hybrida.*
Variety denomination: 'EC-ALOE-1801'.

BACKGROUND OF THE INVENTION

The new cultivar is a product of a planned breeding program. The seed parent is a hybrid from a cross between an unnamed, unpatented *Aloe aculeata* hybrid and the unpatented *Aloe* 'Debora Zimmermann'. The pollen parent is the unpatented *Aloe* hybrid 'Carmine'. The crossing was made in during 2013 in Sappemeer, The Netherlands at a commercial greenhouse. 'EC-ALOE-1801' was discovered by the inventor in 2015.

Asexual reproduction of the new cultivar 'EC-ALOE-1801' was first performed in Sappemeer, The Netherlands, at a commercial laboratory by tissue culture in March 2015. 'EC-ALOE-1801' has since produced several generations and has shown that the unique features of this cultivar are stable and reproduced true to type.

SUMMARY OF THE INVENTION

The cultivar 'EC-ALOE-1801' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-ALOE-1801.' These characteristics in combination distinguish 'EC-ALOE-1801' as a new and distinct *Aloe* cultivar:

1. Green leaves with a distinctive red coloration to marginal serration.
2. Upright foliage aspect with a slight backward curve toward the apical section.

PARENTAL COMPARISON

Plants of the new cultivar 'EC-ALOE-1801' are similar to the seed parent in most horticultural characteristics. However, plants of the new variety differ from the seed parent in the following:

1. New cultivar has a red serrate margin on green leaves, with no dots; seed parent has a pink-red margin and pink-red dots on green leaves.
2. New variety is a larger plant than the seed parent.

Plants of the new cultivar 'EC-ALOE-1801' are similar to the pollen parent in most horticultural characteristics. However, plants of the new variety differ in the following:

1. New cultivar has a red serrate margin on green leaves, the pollen parent has red zigzag rim and red dots on green leaves.
2. New variety is a larger plant than the pollen parent.

COMMERCIAL COMPARISON

'EC-ALOE-1801' can be compared to the unpatented commercial variety *Aloe* 'Christmas Sleigh.' The two *Aloe* varieties are similar in most horticultural characteristics; however, the new variety differs in the following:

1. New cultivar has red marginal serrations on green leaves; this comparator has a red marginal serrations and red dots on blue-green leaves.
2. New cultivar's leaves grow upright, while comparator's leaves form a flat-shaped rosette.
3. New variety's leaves are much more elongated; comparator's leaves are wider at the base, and shorter.

'EC-ALOE-1801' can also be compared to the unpatented commercial variety *Aloe* 'Debora Zimmermann.' The two *Aloe* varieties are similar in most horticultural characteristics; however, the new variety differs in the following:

1. New cultivar has red marginal serrations on green leaves, with no dots; comparator has a pink-red margin and pink-red dots on green leaves.

BRIEF DESCRIPTION OF THE PHOTOGRAPHS

The accompanying photograph in FIG. 1 illustrates in full color a typical flowering plant of 'EC-ALOE-1801' grown in a greenhouse in Sappemeer, The Netherlands. This plant is approximately 25 weeks old, shown in a 10.5 cm container.

Figure 1:
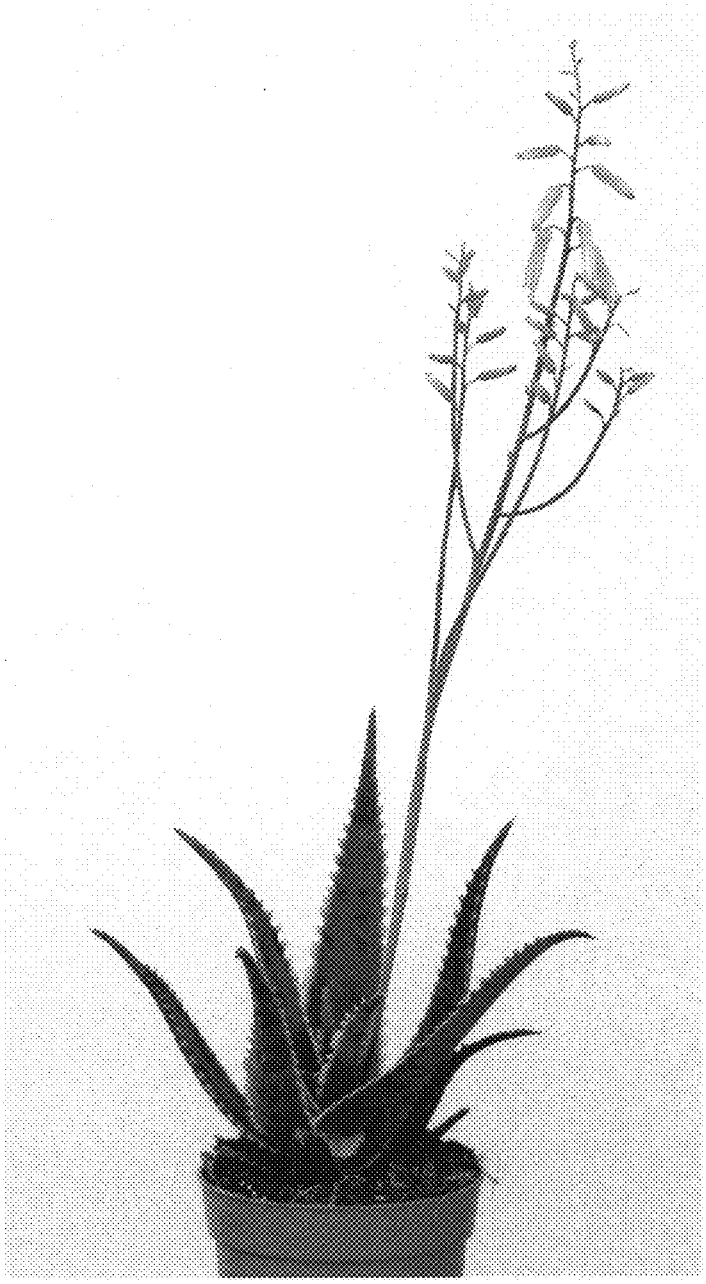
Figure 2:
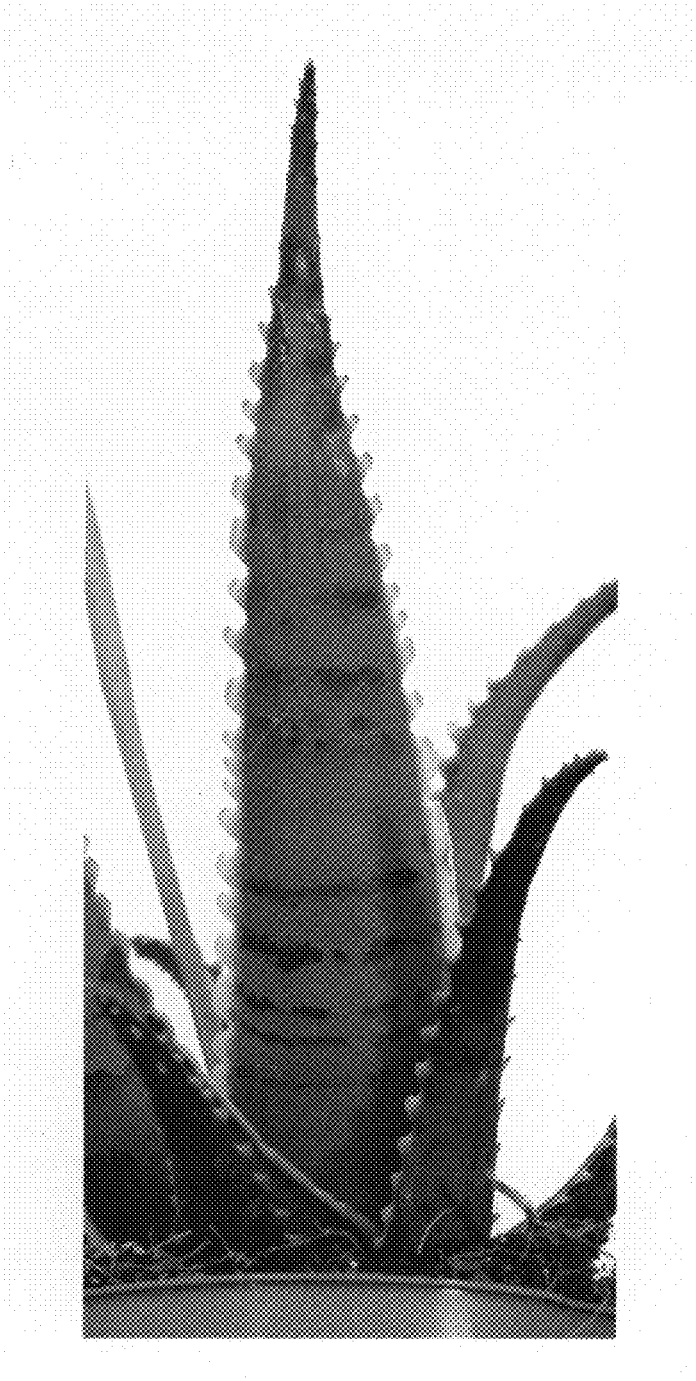
FIG. 2 illustrates a close up view of the underside of the foliage.
Figure 3:
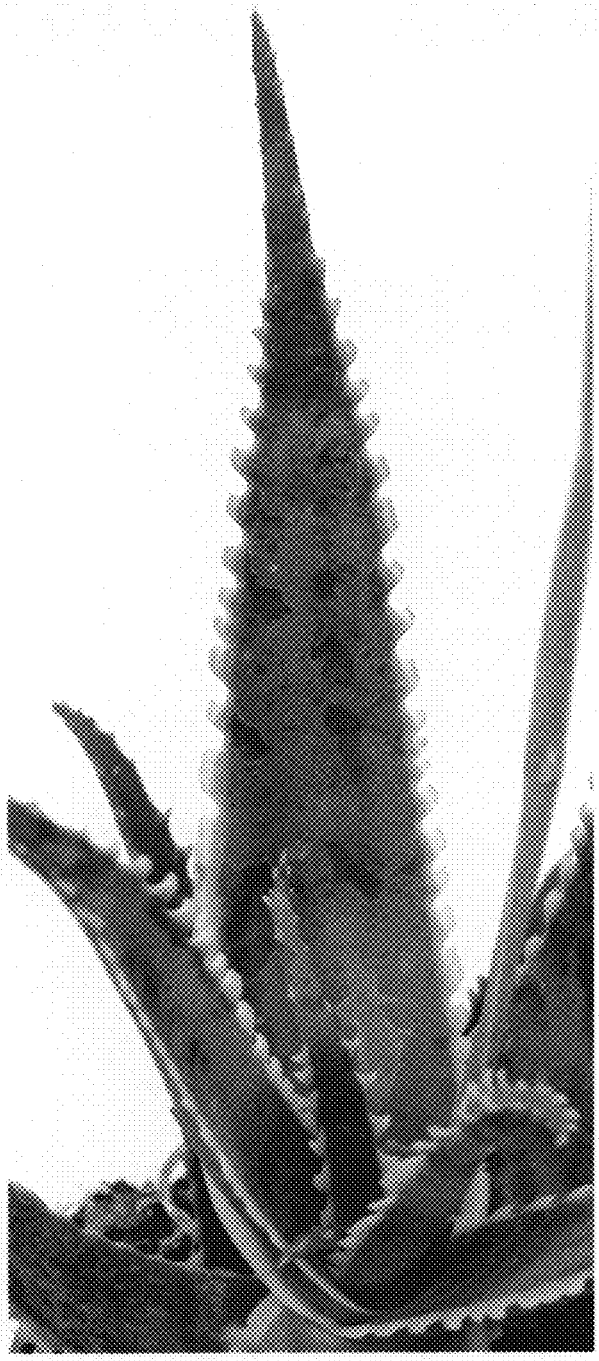
FIG. 3 illustrates a close up view of the upper-side of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Color Chart, 2015 edition, except where general terms of ordinary dictionary significance are used. The following observations and measurements describe 'EC-ALOE-1801' plants in a commercial greenhouse in Sappemeer, The Netherlands. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'EC-ALOE-1801.'.

Age of the plant described: 25 weeks.

PROPAGATION

Time to initiate roots: Approximately 20 to 25 days at 21° C.

Root description: Fibrous. Brown, not accurately measured with the R.H.S. chart.

Propagation method: Tissue culture.

PLANT

Growth habit: Basal rosette of upright leaves with inflorescence carried above the leaf plane.

Container size: 10.5 cm.

Height: 16.7 cm to top of foliar plane.

Plant spread: Approximately 18.9 cm.

Growth rate: Low to moderate.

Branching characteristics: Basal rosettes.

FOLIAGE

Leaf:

- *Arrangement*.—Rosette.
- *Average length*.—14.8 cm.
- *Widest width*.—3.4 cm.
- *Shape of blade*.—Lanceolate, succulent.
- *Apex*.—Long acuminate.
- *Base*.—Broad cuneate.
- *Margin*.—Coarsely and bluntly dentate-serrate.
- *Aspect*.—Upright with a slight outward arch in apical section.
- *Texture of top surface*.—Smooth, glabrous, covered with a thin waxy layer.
- *Texture of bottom surface*.—Smooth, glabrous, covered with a thin waxy layer.
- *Quantity of leaves*.—Approximately 13 per rosette.
- *Color*.—Young foliage upper side: Near RHS Green 139A with waxy layer RHS Greyed-Green N189D. Marginal serrations near Red 41B. Young foliage under side: Near RHS Green 138A with waxy layer RHS Greyed-Green N189D. Marginal serrations near Red 41A. Mature foliage upper side: Between RHS Yellow-Green 147A and Greyed-Green 189A, with margin of Yellow-Green 145B. Waxy layer of Greyed-Green N189C-N189D. Marginal serrations near Red 44C. Mature foliage under side: RHS Yellow-Green 147A, with margin of Yellow-Green 145B. Waxy layer of Greyed-Green N189C-N189D. Marginal serrations near Red 43B.
- *Venation*.—No visible veins.

FLOWER

Natural flowering season: Fall to Winter.

Inflorescence type and habit: Compound raceme.

Time to flower or response time: Average 10 months.

Quantity of flowers per inflorescence: Approximately 42.

Quantity of flowers per plant: 3.

Total inflorescence size:

- *Height*.—Approximately 27.2 cm.
- *Width*.—Approximately 9.5 cm.

Flower bud:

- *Length*.—Approximately 1.6 cm.
- *Width*.—Approximately 0.4 cm.
- *Luster*.—Matte.
- *Texture*.—Smooth, glabrous.
- *Shape*.—Narrow oblong.
- *Color*.—RHS Orange-Red 35C, fading to Yellow 11C-11D towards the top. Outer tip Green N138C.

Flower:

- *Flower type and form*.—Single, tubular.
- *Aspect*.—Nodding.
- *Habit*.—Moderate.
- *Fragrance*.—None.
- *Height*.—0.8 cm.
- *Diameter*.—0.75 cm.
- *Length*.—2.4 cm.
- *Longevity on plant*.—5 days.
- *Persistent or self-cleaning*.—Self-cleaning.

Sepals: No true sepals.

Tepals:

- *Arrangement*.—Rotate, tubular.
- *Number per flower*.—6.
- *Number of whorls*.—1.
- *Tepals fused*.—No.
- *Length*.—2.1 cm.
- *Width*.—0.4 cm.
- *Shape*.—Narrow oblong.
- *Tip*.—Acute.
- *Base*.—Obtuse.
- *Margin*.—Entire.
- *Margin undulation*.—None.
- *Texture, upper and under sides*.—Smooth, glabrous.
- *Rugosity*.—Both sides non-rugose.
- *Luster, upper and under sides*.—Matte.
- *Color when opening, upper side*.—RHS Orange-Red 32C, fading to 36B towards the top. Outer tip Yellow-Green 146B.
- *Color when opening, under side*.—RHS Orange-Red 35C, fading to 36D towards the top. Outer tip Yellow-Green 146B.
- *Color fully opened, upper side*.—RHS Orange-Red 32C, fading to 36B towards the top. Outer tip Yellow-Green 146B.

*Color fully opened, upper side.*—RHS Orange-Red 35C, fading to 36D towards the top. Outer tip Yellow-Green 146B.

*Venation color fully opened, upper and under side.*—RHS Orange 26B.

Calyx:

*Shape.*—Tubular.

*Length.*—2.4 cm.

*Diameter.*—0.8 cm horizontal; 0.75 cm vertical.

Peduncle:

*Length.*—41.6 cm.

*Diameter.*—0.25 cm.

*Angle to lateral branch axis.*—80 degrees.

*Strength.*—Moderate.

*Texture.*—Smooth, glabrous, covered with a thin waxy layer.

*Luster.*—Matte.

*Color.*—RHS Yellow-Green 146A.

Pedicel:

*Length.*—0.7 cm.

*Diameter.*—0.1 cm.

*Angle to peduncle axis.*—45 degrees.

*Strength.*—Moderately strong.

*Texture.*—Smooth, Glabrous.

*Luster.*—Matte.

*Color.*—RHS Greyed-Orange 173B to 173C.

Bracts:

*Shape.*—Deltoid.

*Length.*—0.25 cm.

*Width.*—0.175 cm.

*Margin.*—Entire.

*Top.*—Acute.

*Base.*—Cuneate.

*Color.*—RHS Greyed-White 156D, veined Greyed-Brown 199B to 199D.

REPRODUCTIVE ORGANS

Stamens:

*Number.*—Average 6.

*Filament length.*—2.2 cm.

*Filament color.*—RHS Green-Yellow 1D, fading to White NN155A towards base.

*Anther length.*—0.2 cm.

*Anther color.*—RHS Brown 200A.

*Anther shape.*—Narrow oblong, dorsifixed.

*Pollen.*—RHS Orange-Red 35C.

Pistil:

*Number.*—1.

*Length.*—Approximately 1.8 cm.

*Style color.*—RHS Yellow-Green 154C, fading lighter towards the base to Yellow-Green 150D.

*Stigma.*—Shape: Pointed. Color: RHS Yellow-Green 150C. Ovary color: RHS Yellow-Green N144B.

OTHER CHARACTERISTICS

Seeds and fruits: None observed to date.

Temperature tolerance: Tolerates temperatures up to 40 degrees C.

Disease/pest resistance: Neither resistance nor susceptibility to normal diseases and pests known to *Aloe* observed to date.

What is claimed is:

1. A new and distinct cultivar of *Aloe* plant named 'EC-ALOE-1801' as herein illustrated and described.

* * * * *